United States Patent
Peterson et al.

(10) Patent No.: US 6,990,411 B2
(45) Date of Patent: Jan. 24, 2006

(54) CONTROLLING CHEMICAL DISPENSE OPERATIONS BASED ON CONDUCTIVITY OFFSET CONSIDERATIONS

(75) Inventors: Jeff W. Peterson, Hudson, WI (US); Ronald Bruce Howes, Jr., Minneapolis, MN (US); Robert Eugene May, Lakeville, MN (US)

(73) Assignee: Ecolab, Inc., St. Paul, MN (US)

( * ) Notice: Subject to any disclaimer, the term of this patent is extended or adjusted under 35 U.S.C. 154(b) by 0 days.

(21) Appl. No.: 11/004,478

(22) Filed: Dec. 3, 2004

(65) Prior Publication Data

US 2005/0149273 A1    Jul. 7, 2005

Related U.S. Application Data

(63) Continuation-in-part of application No. 10/444,823, filed on May 22, 2003, now Pat. No. 6,892,143.

(51) Int. Cl.
    *G01N 31/00* (2006.01)
(52) U.S. Cl. .................... 702/31; 702/22; 702/30; 700/9; 700/80
(58) Field of Classification Search .............. 702/31, 702/25, 30, 22–23; 700/9, 80, 239, 265, 700/283; 340/853.3, 853.2, 870.07; 705/1
See application file for complete search history.

(56) References Cited

U.S. PATENT DOCUMENTS

| | | |
|---|---|---|
| 3,223,108 A | 12/1965 | Martz, Jr. |
| 3,645,669 A | 2/1972 | Rausch |
| 3,774,056 A | 11/1973 | Sample et al. |
| 4,194,242 A | 3/1980 | Robbins |
| 4,241,400 A | 12/1980 | Kiefer |
| 4,334,270 A | 6/1982 | Towers |
| 4,482,785 A | 11/1984 | Finnegan et al. |
| 4,509,543 A | 4/1985 | Livingston et al. |
| 4,597,046 A | 6/1986 | Musmanno et al. |
| 4,682,113 A | 7/1987 | Barben, II |
| 4,733,798 A | 3/1988 | Brady et al. |
| 4,739,478 A | 4/1988 | Roberts et al. |

(Continued)

FOREIGN PATENT DOCUMENTS

GB    1508469    4/1978

OTHER PUBLICATIONS

U.S. Appl. No. 09/692,550, filed Oct. 19, 2000, Howes, Jr. et al.
"Services Provided by Jaytech, Inc.", at http://www.jaytech.com, 2 pages.
Clover Systems Inc.'s product description of InfAc, 4 pages, including specifications and features.
International Search Report dated Oct. 4, 2004.

*Primary Examiner*—John Barlow
*Assistant Examiner*—Hien Vo
(74) *Attorney, Agent, or Firm*—Merchant & Gould

(57) ABSTRACT

A system and method is disclosed for controlling concentration of a component chemical product in a chemical solution. The chemical solution is formed in a solution tank by combining the component chemical product with water. The component chemical product is dispensed to the solution tank by a chemical dispenser that is controlled by measured conductivity readings of the chemical solution taken in the solution tank. The conductivity readings are analyzed against a conductivity setpoint to determine whether the component chemical product should be added to the chemical solution. A conductivity offset is determined and applied to the analysis thereby taking into consideration any conductivity that may be attributable to constituents of the chemical solution other than the component chemical product. Such constituents include soil washed from the articles and the water used to form the chemical solution.

40 Claims, 7 Drawing Sheets

U.S. PATENT DOCUMENTS

| | | |
|---|---|---|
| 4,756,321 A | 7/1988 | Livingston et al. |
| 5,014,211 A | 5/1991 | Turner et al. |
| 5,038,807 A | 8/1991 | Bailey et al. |
| 5,043,860 A | 8/1991 | Koether et al. |
| 5,077,525 A | 12/1991 | Okel et al. |
| 5,203,366 A | 4/1993 | Czeck et al. .................. 137/3 |
| 5,222,027 A | 6/1993 | Williams et al. ............ 700/239 |
| 5,345,379 A | 9/1994 | Brous et al. .................. 700/17 |
| 5,370,267 A | 12/1994 | Schroeder |
| 5,370,743 A | 12/1994 | Usui et al. |
| 5,397,028 A | 3/1995 | Jesadanont |
| 5,404,893 A | 4/1995 | Brady et al. |
| 5,491,791 A | 2/1996 | Glowney et al. |
| 5,556,478 A | 9/1996 | Brady et al. |
| 5,625,659 A | 4/1997 | Sears |
| 5,625,908 A | 5/1997 | Shaw |
| 5,681,400 A | 10/1997 | Brady et al. ................... 134/18 |
| 5,694,323 A | 12/1997 | Koropitzer et al. ......... 705/400 |
| 5,695,091 A | 12/1997 | Winings et al. |
| 5,724,261 A | 3/1998 | Denny et al. |
| 5,745,381 A | 4/1998 | Tanaka et al. .............. 702/182 |
| 5,757,664 A | 5/1998 | Rogers et al. .............. 700/232 |
| 5,810,201 A | 9/1998 | Besse et al. |
| 5,826,749 A | 10/1998 | Howland et al. ............... 222/1 |
| 5,839,097 A | 11/1998 | Klausner ............... 340/825.69 |
| 5,875,430 A | 2/1999 | Koether |
| 5,939,974 A | 8/1999 | Heagle et al. |
| 5,945,910 A | 8/1999 | Gorra |
| 5,956,487 A | 9/1999 | Venkatraman et al. |
| 5,967,202 A | 10/1999 | Mullen et al. .............. 141/104 |
| 5,973,696 A | 10/1999 | Agranat et al. |
| 5,975,352 A | 11/1999 | Spriggs et al. ................ 222/23 |
| 5,980,090 A | 11/1999 | Royal et al. ................ 700/241 |
| 6,003,070 A | 12/1999 | Frantz |
| 6,061,668 A | 5/2000 | Sharrow .................... 705/400 |
| 6,133,555 A | 10/2000 | Brenn |
| 6,133,847 A | 10/2000 | Yang |
| 6,321,204 B1 | 11/2001 | Kazami et al. ................. 705/7 |
| 6,330,499 B1 | 12/2001 | Chou et al. |
| 6,356,205 B1 | 3/2002 | Salvo et al. |
| 6,357,292 B1 | 3/2002 | Schultz et al. |
| 6,377,868 B1 | 4/2002 | Gardner .................... 700/236 |
| 6,389,464 B1 | 5/2002 | Krishnamurthy et al. |
| 6,498,567 B1 | 12/2002 | Grefenstette et al. |
| 6,618,754 B1 | 9/2003 | Gosling |
| 2001/0039501 A1 | 11/2001 | Crevel et al. |
| 2001/0047214 A1 | 11/2001 | Cocking et al. |
| 2001/0053939 A1 | 12/2001 | Crevel et al. |
| 2001/0054038 A1 | 12/2001 | Crevel et al. |

CONTROLLING CHEMICAL DISPENSE OPERATIONS BASED ON CONDUCTIVITY OFFSET CONSIDERATIONS

RELATED APPLICATIONS

This application is a continuation-in-part of U.S. patent application for "CONTROLLING CHEMICAL DISPENSE OPERATIONS BASED ON A CONDUCTIVITY OFFSET," filed on May 22, 2003 and assigned Ser. No. 10/444,823, now U.S. Pat. No. 6,892,143 the complete disclosure of which is hereby incorporated by reference in its entirety.

TECHNICAL FIELD

The invention relates generally to a chemical dispenser, and more particularly to controlling operation of the chemical dispenser based on conductivity measurements of chemical solutions formed by the dispenser.

BACKGROUND

A warewash machine is a utility dishwasher used in many restaurants, healthcare facilities and other locations to efficiently clean and sanitize cooking and eating articles, such as, dishes, pots, pans, utensils and other cooking equipment. Soiled articles are placed on racks and provided to a washing chamber of the warewash machine. In the chamber, cleaning products and a rinse agent are applied to the articles over a predefined period of time referred to as a "wash cycle," which includes a cleaning cycle and a rinsing cycle. The cleaning products are typically chemical solutions formed by dissolving one or more component chemical products in the rinse agent. The term component chemical product is used broadly herein to encompass, without limitation, any type of detergent, soap or any other product used for cleaning and/or sanitizing. The rinse agent typically is water, and may include wetting and/or sanitizing agents.

The article racks contain holes that enable the cleaning product, the rinse agent and soil washed from the articles to pass through the racks during the wash cycle and to a solution tank located on the underside of the warewash machine. At the end of the wash cycle, the rack is removed from the washing chamber so that other racks carrying other soiled articles may be moved into the washing chamber. The wash cycle is then repeated for each of these subsequent racks. Wash cycles may be customized for specific types of racks and the articles that the racks carry.

The cleaning product (hereinafter, "chemical solution") is formed within the solution tank from the combination of the rinse agent, which initially is dispensed into the solution tank prior to the introduction of any article racks and subsequently dispensed thereto during the rinsing cycles, and a component chemical product directly input to the solution tank. A wash module is provided above the solution tank and in the lower portion of the washing chamber. The wash module extracts the chemical solution from the tank and applies the solution to the rack (and hence, the articles contained therein) during the cleaning cycle. Following the cleaning cycle, a rinse module, which is provided in the upper portion of the washing chamber, administers the rinsing cycle by applying a rinse agent to the articles thereby rinsing the chemical solution from the articles. During both the cleaning and rinsing cycles soil (e.g., food particles) is dislodged from the articles in the racks and washed into the solution tank to combine with the chemical solution.

Percent concentration of each individual component chemical product within a chemical solution being used by a warewash machine to clean and sanitize articles at a public facility is governed by various food and health regulations. The percent concentration of a particular component chemical product relative to a formed chemical solution is proportional to the mass of the component relative to the mass of the rinse agent in the chemical solution. One generally accepted method for complying with these regulations involves controlling input of the component chemical product to the solution tank based on conductivity measurements of the chemical solution. These conductivity measurements generally represent the electrical behavior of the chemical solution, i.e., the ionic concentration of the solution relative to pure water.

To meet the above-noted various food and health regulations, warewash controllers are employed to oversee operations performed during the wash cycles of conventional warewash machines. Warewash controllers are often added to warewash machines after the machines are deployed into a production environment in which the machines are intended for use. The warewash controllers are communicatively coupled to the rinse and wash modules such that control over operations of these modules is administered by the controller. The warewash controller may also be communicatively coupled to a component dispenser and operable to control the component dispenser to dispense specified amounts of a component chemical product to the solution tank and/or wash chamber. Alternatively, the controller for the component dispenser may be separate from the warewash controller. Regardless of implementation, the basic function for controlling the component dispenser involves sensing information related to operation of the warewash machine and using this sensed information to operate the component dispenser in such a manner that the various food and health regulations are complied with.

Inductive probes or conductivity cells may both be used to measure the ionic concentration of a chemical solution within the solution tank. Typically, these probes or cells gather such information by sampling, preferably multiple times, the chemical solution in the solution tank to generate therefrom an electrical parameter (e.g., conductance or resistance) indicative of the ionic concentration of the chemical solution relative to pure water. This electrical parameter renders an associated conductivity reading for the chemical solution. The associated conductivity reading represents an estimated percent concentration of the component chemical product relative to the rinse agent in the chemical solution. Based on this calculation, the controller controlling the component dispenser controls the dispensing of the component chemical product in order to force the percent concentration of that component chemical product in the chemical solution to a level prescribed by governing regulations.

While using conductivity measurements to control product concentration in a chemical solution has proven to be an effective practice for complying with the various governing food and health regulations, these conductivity measurements are not entirely accurate readings of the actual percent concentration of the product in the solution. In addition to ions associated with the component chemical product, a chemical solution typically includes ions associated with the water used for the rinse agent as well as ions associated with the soil washed from the articles placed in the warewash machine. Both water and soil therefore contribute to the ionic concentration of a particular chemical solution, and as such the determined conductivity is not a true measure of the percent concentration of a component chemical product contained in the solution.

SUMMARY OF THE INVENTION

In accordance with the present invention, the above and other problems are solved a method for controlling concentration of a chemical product in a chemical solution by taking into consideration one or more offsets representing portion(s) of measured conductivity readings for the chemical solution that are attributable to components of the solution other than the chemical product. For example, one such offset may represent a portion of the measured conductivity readings attributable to any soil in the solution. Another such offset may represent the inherent conductivity of water used to form the chemical solution. Even further, the present invention contemplates taking into consideration both of the aforementioned water and soil offsets while controlling concentration of a component chemical product within a chemical solution.

In accordance with an embodiment, the present invention is practiced as a method performed in a computer system. In this embodiment, the method includes an act of determining a conductivity measurement for the chemical solution. The conductivity measurement indicates a percent concentration of the component chemical product in the chemical solution. The method also includes an act of determining a conductivity offset value that represents a portion of the conductivity measurement that is attributable to one or more constituents of the chemical solution other than the component chemical product. The constituents may be soil that washes into the chemical solution by virtue of a washing process or water used to form the chemical solution. Other constituents are also contemplated within the scope of the present invention. The method yet further includes analyzing the conductivity offset value, the conductivity measurement and a conductivity setpoint indicating a desired percent concentration of the component chemical product in the chemical solution to determine whether the component chemical product should be added to the chemical solution.

In accordance with another embodiment, the present invention is practiced as a method performed in a computer system and the chemical solution is contained in a solution tank and used by a utility device to clean and sanitize articles having soil deposited thereon. The utility device applies the chemical solution to the articles thereby washing the soil and applied chemical solution into the solution tank. As such, the soil mixes with the chemical solution in the tank, and consequently, contributes to the conductivity of the chemical solution contained therein.

In this embodiment, the method includes an act of determining a conductivity measurement for the chemical solution. The conductivity measurement indicates a percent concentration of the component chemical product in the chemical solution. The method also includes an act of determining a soil conductivity offset value that represents a portion of the conductivity measurement that is attributable to the soil mixed into the chemical solution. The method yet further includes analyzing the soil conductivity offset value, the conductivity measurement and a conductivity setpoint indicating a desired percent concentration of the chemical product in the chemical solution to determine whether the chemical product should be added to the chemical solution.

Various methods may be used to analyze a conductivity offset value, a conductivity measurement for a solution and a conductivity setpoint defined for the solution. One such method is to normalize the conductivity measurement by the conductivity offset value by subtracting the conductivity offset value from the conductivity measurement and comparing the normalized conductivity reading to the conductivity setpoint. Using this method, the present invention requests that a specified volume of component chemical product be supplied to the solution tank if the normalized conductivity reading is less than the conductivity setpoint. Another such method is to normalize the conductivity setpoint by adding the conductivity offset value to the conductivity setpoint and comparing the conductivity measurement of the chemical solution to the normalized conductivity setpoint. Using this method, the present invention requests that a specified volume of component chemical product be supplied to the solution tank if the normalized conductivity setpoint is greater than the conductivity reading.

The invention may be implemented as a computer process, a computing system or as an article of manufacture such as a solid state, non-volatile memory device or a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process.

These and various other features as well as advantages, which characterize the present invention, will be apparent from a reading of the following detailed description and a review of the associated drawings.

DETAILED DESCRIPTION

Figure 1:
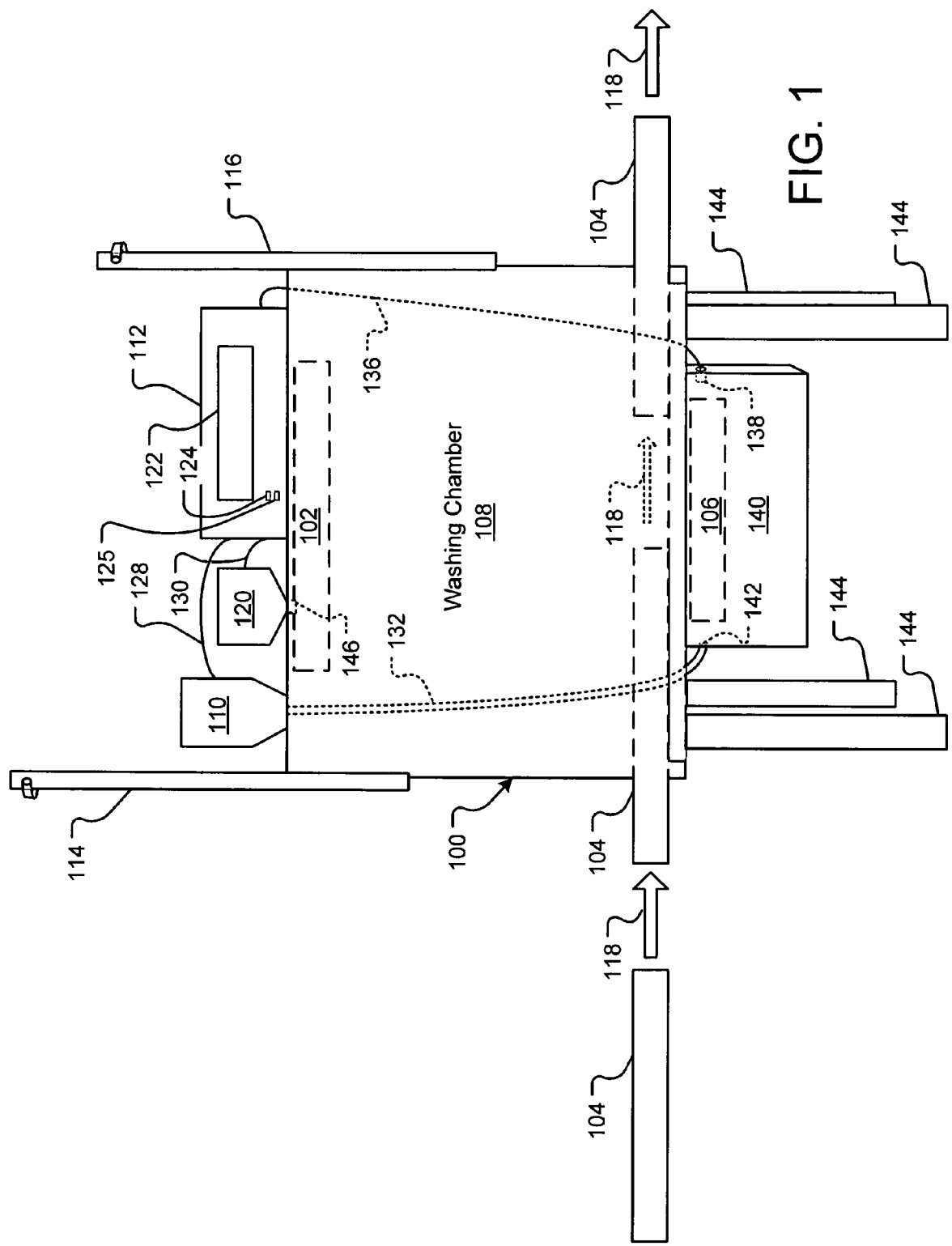
FIG. 1 illustrates components of a utility device in accordance with an embodiment of the present invention.

The present invention and its various embodiments are described in detail below with reference to the figures. When referring to the figures, like structures and elements shown throughout are indicated with like reference numerals.

Objects depicted in the figures that are covered by another object, as well as the reference annotations thereto, are shown using dashed lines.

In one embodiment, the present invention relates to measuring a conductivity offset for use in normalizing conductivity readings of a chemical solution being used or applied (to articles) by a utility device. In another embodiment, the present invention relates to controlling dispensing operations for a component chemical product based on the normalized conductivity reading. In either embodiment of the invention, the chemical solution is a cleaning product used by a utility device to clean and/or sanitize articles placed in or around the device. The chemical solution is defined herein as a combination of at least one component chemical product and water. In accordance with this embodiment, the utility device is described below as being a cleaning apparatus, and more particularly a commercial dishwasher, which is also referred to as a "warewash machine."

Referring now to FIG. 1, a warewash machine 100 is shown in accordance with an embodiment of the present invention. The warewash machine 100 is used to clean all types of dishware and kitchen articles, such as, without limitation, pots and pans used in restaurants, cafeterias and bakeries. The articles are provided to the warewash machine 100 on article racks 104. The warewash machine 100 may be any type of warewash machine, such as, without limitation, a conveyor-type warewash machine, a flight-type warewash machine, a recirculating door-type warewash machine, or a commercial dump or fill-type dish machine. For illustrative purposes, however, the warewash machine 100 is described as being a conveyor-type warewash machine with standard article racks 104. It should be appreciated that cleaning apparatus other than warewash machines may be employed, including, for example, laundry machines and animal cage washers used in animal research areas.

The warewash machine 100 includes a washing chamber 108, which, in the embodiment shown is enclosed by an entry sliding door 114 and an exit sliding door 116. The washing chamber 108 is supported above ground level by a plurality of legs 144. In operation, each article rack 104 carries one or more articles to be washed by the warewash machine 100 into the washing chamber 108 through an opened entry sliding door 114. Arrows 118, which are provided in FIG. 1 for illustration purposes only, show the direction of article racks 104 through the washing chamber 108 in accordance with an embodiment of the present invention. Once an article rack 104 is located inside the washing chamber 108, the entry sliding door 114 and the exit sliding door 116 are both closed to fully contain the washing chamber 108 on all sides.

A rinse module 102 is provided within or directly above the washing chamber 108 for applying a rinse agent to articles placed in the article racks 104. Water is hereinafter described as the exemplary rinse agent in accordance with an embodiment of the present invention. The water may include wetting agent(s) and/or sanitizing agent(s) dissolved therein. A wash module 106 is provided within or directly below the washing chamber 108 for applying a chemical solution to articles placed in the racks 104. The chemical solution cleans the articles for subsequent use in eating, cooking or otherwise utilizing. In an embodiment, the rinse module 102 and the wash module 106 include arms (not shown) operably mounted to a spindle (not shown) for rotation about the spindle axis. The arms of the rinse module 102 include a plurality of openings (not shown) through which water is passed to articles placed in the washing chamber 108. Likewise, the arms of the wash module 106 include a plurality of openings (not shown) through which the chemical solution is passed to articles placed in the washing chamber 108.

The chemical solution is formed and stored in a solution tank 140 positioned underneath the washing chamber 108. The chemical solution is formed as a combination of water provided by the rinse module 102 and one or more component chemical products. For illustration purposes, and not by means of limitation, the chemical solution formed in the solution tank 140 is a combination of a single component chemical product and water.

A drain (not shown) is positioned within the solution tank 140 to enable the flow of used chemical solution out of the solution tank 140 and into a chemical waste system, such as a septic tank or sewer. The act of removing the chemical solution from the solution tank 140 is referred to as "flushing." In accordance with various embodiments, the chemical solution may be automatically flushed after each wash cycle or after a predetermined number of wash cycles, or alternatively, some warewash machines may only allow manual flushing through the drain. The embodiment employed is a matter of implementation and it should therefore be appreciated that any means for flushing solution out of the solution tank 140 is contemplated within the scope of the present invention.

Prior to being provided to the solution tank 140, the component chemical product used to form the chemical solution is stored in a product reservoir 110 in either a solid or liquid form. If the component chemical product is stored as a solid, water is applied to the product to liquefy the component chemical product such that the product may be provided to the solution tank 140 by way of a supply hose 132. Water is stored in a water reservoir 120 and dispensed into the washing chamber 108 by the rinse module 102. Water passes from the water reservoir 120 to the rinse module 102 by way of a coupling 146 therebetween. The rinse module 102 then applies the water to articles contained in a rack 104 situated in the washing chamber 108. An opening (not shown) is provided between the solution tank 140 and the washing chamber 108 to allow water and soil to enter the solution tank 140. Water provided to the washing chamber 108 by the rinse module 102 passes through the opening into the solution tank 140, therein combining with pre-existing chemical solution to further dilute the chemical solution and therefore lower the concentration of component chemical product in the solution.

Dispensing of the component chemical product to the solution tank 140 is controlled by a controller. The controller is embodied in software or firmware contained within a control box 112, as shown in an exemplary embodiment illustrated in FIG. 1. As described below, the control box 112 includes inputs for use by the controller in monitoring operation of the warewash machine 100 and outputs for controlling dispensing of the component chemical product thereto. For example, in response to detecting initiation of a wash cycle for each rack 104 provided to the warewash machine 100, the controller controls dispensing of the component chemical product to the solution tank 140. To accomplish this, the warewash controller measures conductivity of the chemical solution resident in the solution tank 140, and based on this measurement, controls the amount of the component chemical product dispensed to the solution tank 140. In an exemplary embodiment, the controller is a special-purpose controller manufactured by NOVA Controls. However, it should be appreciated that the controller may be any type or make of controller—analog-based, digital-based or a combination of both—known to those skilled in the art.

The control box 112 may also include one or more display devices or modules, such as, without limitation, first and second status indicators, e.g., light emitting diodes (LED's) 124 and 125, and a graphical user interface (GUI) 122. Various type of information relative to the current operation of the controller are displayed by these display devices. For example, any one of these display devices 122, 124 and/or 125 may indicate to a user of the warewash machine 100 that the component chemical product is currently being dispensed to the solution tank 140. Further, the GUI 122 may support functionality for authorizing a user access to input information into the controller. For instance, the GUI 122 may present a graphical selection screen that enables a user to define or modify the conductivity setpoint value for the chemical solution.

In accordance with an embodiment of the present invention, the controller may also control and/or monitor various tasks administered by the warewash machine 100 over a given wash cycle in addition to controlling component product dispensing. In this embodiment, the controller thus controls operation of the rinse module 102 and the wash module 106 during each wash cycle performed by the warewash machine 100. As such, the display devices 122, 124 and/or 125 may be used to display information regarding and/or provide a user interface for controlling any task related to operation of the warewash machine 100.

In accordance with these various embodiments, the controller administers the aforementioned control and monitoring operations using a chemical product output control line 128, a water output control line 130 and/or a conductivity input control line 136, each input to the control box 112. The chemical product output control line 128 couples the control box 112 to a processor (not shown) responsible for dispensing the component chemical product from the product reservoir 110. Under direction of the controller, the control box 112 transmits signals to the product reservoir processor over the chemical product output control line 128. These signals direct the product reservoir processor to dispense a particular volume of chemical product to the solution tank 140. If the component chemical product is stored in the product reservoir 110 in a solid form, the product reservoir processor activates a water pump that applies a predetermined volume of water to the solidified chemical product. Upon the application of this predetermined volume of water, an associated volume (with respect to the predetermined volume of water) of the component chemical product in a liquid form is created and dispensed out of the product reservoir 110.

The water output control line 130 couples the control box 112 to a processor (not shown) responsible for dispensing water from the water reservoir 120. In an embodiment, the water reservoir processor controls operation of a water pump (not shown) that pushes water through an output of the water reservoir 120 and into the rinse module 102. Under direction of the controller, the control box 112 transmits signals to the water reservoir processor over the water output control line 130. These signals direct the water reservoir processor to activate the water pump to dispense a predetermined volume of water to the rinse module 102. Almost simultaneously and under the direction of the controller in accordance with an embodiment described above, the control box 112 also directs the rinse module 102 to provide the water to the washing chamber 108 for application to articles contained in an article rack 104 currently situated therein. The water passes over the articles and to the solution tank 140, where the water combines with chemical solution already contained in the tank 140, thereby diluting the solution.

As the chemical solution resides in the solution tank 140, the controller monitors concentration of the component chemical product within the chemical solution based on conductivity measurements. To accomplish this, the conductivity input control line 136 couples the control box 112 to an inductive probe 138 operable for sensing information, e.g., electrical properties, for use in determining the conductivity of the chemical solution. This sensed information, which is provided to the control box 112 over the conductivity input control line 136, is used by the controller to calculate conductivity of the chemical solution. The mathematical relationships used to convert sensed electrical properties, such as conductance and resistance, into an associated conductivity measurement are well known in the art and therefore not addressed with any greater detail.

Each conductivity reading represents an associated percent concentration of the component chemical product in the chemical solution. A target, or setpoint, conductivity reading (hereinafter "conductivity setpoint") represents the desired percent concentration of the component chemical product in the chemical solution. The controller compares the conductivity setpoint to each conductivity measurement to determine whether, and if so, how much, component chemical product should be added to the solution to meet the conductivity setpoint, and thus, the desired percent concentration.

Inductive probes and the methods used by inductive probes to measure conductivity are well known in the art and not described in further detail herein. In an exemplary embodiment, the inductive probe 138 is a Model 28.740.7, manufactured by Lang Apparatebau GmbH. However, it should be appreciated that the inductive probe 138 may be any type or make of inductive probe known to those skilled in the art. Furthermore, the inductive probe 138 may be replaced in an alternative embodiment by one or more conductivity cells. For example, U.S. Pat. No. 4,733,798 teaches conventional electrode-bearing conductivity cells and electrode-less conductivity cells as well as use thereof in measuring conductivity of a chemical solution and controlling concentration of the component chemical product(s) contained therein.

As noted above, an embodiment involves the controller controlling operation of the rinse module 102 and the wash module 106. In this embodiment, the control box 112 is coupled to the rinse module 102 and the wash module 106 by way of communication links (not shown). Under direction of the controller, the control box 112 issues command signals to a processor (not shown) locally controlling the rinse module 102 and a processor (not shown) locally controlling the wash module 106. The command signals are transmitted to the processor over the aforementioned communication links. Based on such control, the controller can determine when either the wash module 106 or the rinse module 102 are currently active, and therefore dispensing the chemical solution or water, respectively, to the washing chamber 108.

Operation of the warewash machine 100 commences after both the entry sliding door 114 and the exit sliding door 116 are closed with a rack 104 being located substantially underneath the rinse module 102 and substantially above the wash module 106. Initially, the chemical solution is applied to the articles by the wash module 106. Application of the chemical solution to the articles is then maintained for a predetermined period in time. After the chemical solution 106 is applied to the articles, the rinse module 102 applies water to the articles in order to rinse the chemical solution away from the articles.

Like the wash module 106, the rinse module 102 is operated for a predetermined period in time. In an embodiment in which the controller in the control box 112 is responsible for controlling and monitoring operations of the wash module 106 and the rinse module 102. That is, the controller initiates both the wash module 106 and the rinse module 102 and controls the length in time that the chemical solution and rinse agent, respectively, are applied thereby. In another embodiment, the wash module 106 and the rinse module 102 are controlled by a dedicated "warewash" controller and the controller in the control box 112 only monitors operation of these modules 106 and 102. Such monitoring is administered in this embodiment in order to perform the various other operations that the controller is responsible for, such as, without limitation, measuring conductivity and determining when and how much component chemical product to dispense to the tank 140. After the wash cycle is complete, the exit sliding door 116 is opened and the rack 104 may be removed from the washing chamber 108 to make the warewash machine 100 available for use by subsequent article racks 104.

Figure 2:
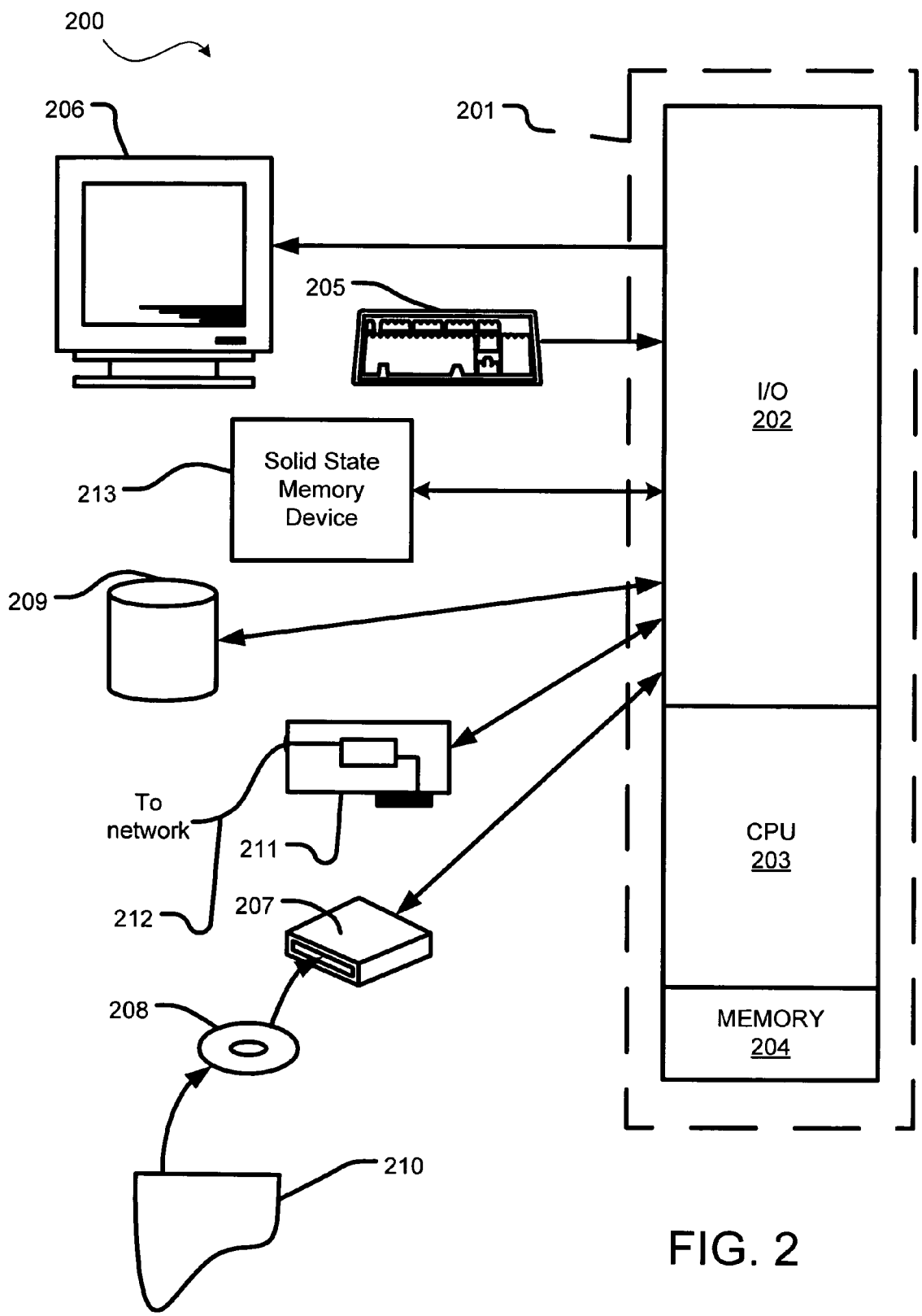
FIG. 2 depicts a general-purpose computer that implements logical operations of an embodiment of the present invention.

FIG. 2 depicts a computing system 200 capable of executing a program product embodiment of the present invention. One operating environment in which the present invention is potentially useful encompasses the computing system 200, such as, for example, the control box 112 or a remote computer to which information collected by the control box 112 may be uploaded. In such a system, data and program files may be input to the computing system 200, which reads the files and executes the programs therein. Some of the elements of a computing system 200 are shown in FIG. 2 wherein a controller, illustrated as a processor 201, is shown having an input/output (I/O) section 202, a microprocessor, or Central Processing Unit (CPU) 203, and a memory section 204. The present invention is optionally implemented in software or firmware modules loaded in memory 204 and/or stored on a solid state, non-volatile memory device 213, a configured CD-ROM 208 or a disk storage unit 209. As such, the computing system 200 is used as a "special-purpose" machine for implementing the present invention.

The I/O section 202 is connected to a user input module 205, e.g., a keyboard, a display unit 206 and one or more program storage devices, such as, without limitation, the solid state, non-volatile memory device 213, the disk storage unit 209, and the disk drive unit 207. The user input module 205 is shown as a keyboard, but may also be any other type of apparatus for inputting commands into the processor 201. The solid state, non-volatile memory device 213 is an embedded memory device for storing instructions and commands in a form readable by the CPU 203. In accordance with various embodiments, the solid state, non-volatile memory device 213 may be Read-Only Memory (ROM), an Erasable Programmable ROM (EPROM), Electrically-Erasable Programmable ROM (EEPROM), a Flash Memory or a Programmable ROM, or any other form of solid state, non-volatile memory. In accordance with one embodiment, the disk drive unit 207 is a CD-ROM driver unit capable of reading the CD-ROM medium 208, which typically contains programs 210 and data. Computer program products containing mechanisms to effectuate the systems and methods in accordance with the present invention may reside in the memory section 204, the solid state, non-volatile memory device 213, the disk storage unit 209 or the CD-ROM medium 208.

In accordance with an alternative embodiment, the disk drive unit 207 may be replaced or supplemented by a floppy drive unit, a tape drive unit, or other storage medium drive unit. A network adapter 211 is capable of connecting the computing system 200 to a network of remote computers via a network link 212. Examples of such systems include SPARC systems offered by Sun Microsystems, Inc., personal computers offered by IBM Corporation and by other manufacturers of IBM-compatible personal computers, and other systems running a UNIX-based or other operating system. A remote computer may be a desktop computer, a server, a router, a network PC (personal computer), a peer device or other common network node, and typically includes many or all of the elements described above relative to the computing system 200. Logical connections may include a local area network (LAN) or a wide area network (WAN). Such networking environments are commonplace in offices, enterprise-wide computer networks, intranets, and the Internet.

In accordance with a program product embodiment of the present invention, software instructions stored on the solid state, non-volatile memory device 213, the disk storage unit 209, or the CD-ROM 208 are executed by the CPU 203. In this embodiment, these instructions may be directed toward communicating data between a client and a server, detecting product usage data, analyzing data, and generating reports. Data is stored in the memory section 204, or on the solid state, non-volatile memory device 213, the disk storage unit 209, the disk drive unit 207 or other storage medium units coupled to the system 200.

In accordance with one embodiment, the computing system 200 further comprises an operating system and usually one or more application programs. Such an embodiment is familiar to those of ordinary skill in the art. The operating system comprises a set of programs that control operations of the computing system 200 and allocation of resources. The set of programs, inclusive of certain utility programs, also provide a graphical user interface to the user. An application program is software that runs on top of the operating system software and uses computer resources made available through the operating system to perform application specific tasks desired by the user. In accordance with an embodiment, the operating system employs a GUI 122 wherein the display output of an application program is presented in a rectangular area on the screen of the display device 206. The operating system is operable to multitask, i.e., execute computing tasks in multiple threads, and thus may be any of the following: Microsoft Corporation's "WINDOWS 95," "WINDOWS CE," "WINDOWS 98," "WINDOWS 2000" or "WINDOWS NT" operating systems, IBM's OS/2 WARP, Apple's MACINTOSH OSX operating system, Linux, UNIX, etc.

In accordance with the practices of persons skilled in the art of computer programming, the present invention is described below with reference to acts and symbolic representations of operations that are performed by the computing system 200, i.e., the control box 112 or a remote computer, unless indicated otherwise. Such acts and operations are sometimes referred to as being computer-executed. It will be appreciated that the acts and symbolically represented operations include the manipulations by the CPU 203 of electrical signals representing data bits causing a transformation or reduction of the electrical signal representation, and the maintenance of data bits at memory locations in the memory 204, the solid state, non-volatile memory device 213, the configured CD-ROM 208 or the storage unit 209 to thereby reconfigure or otherwise alter the operation of the computing system 200, as well as other processing signals. The memory locations where data bits are maintained are physical locations that have particular electrical, magnetic, or optical properties corresponding to the data bits.

The logical operations of the various embodiments of the present invention are implemented either manually and/or (1) as a sequence of computer-implemented steps running on a computing system, e.g., control box 112, and/or (2) as interconnected machine modules within the computing system. The implementation is a matter of choice dependent on the performance requirements of the computing system implementing the invention. Accordingly, the logical operations making up the embodiments of the present invention described herein are referred to alternatively as operations, acts, steps or modules. It will be recognized by one skilled in the art that these operations, structural devices, acts and modules may be implemented in software, in firmware, in special purpose digital logic, and any combination thereof without deviating from the spirit and scope of the present invention as recited within the claims attached hereto.

Figure 3:
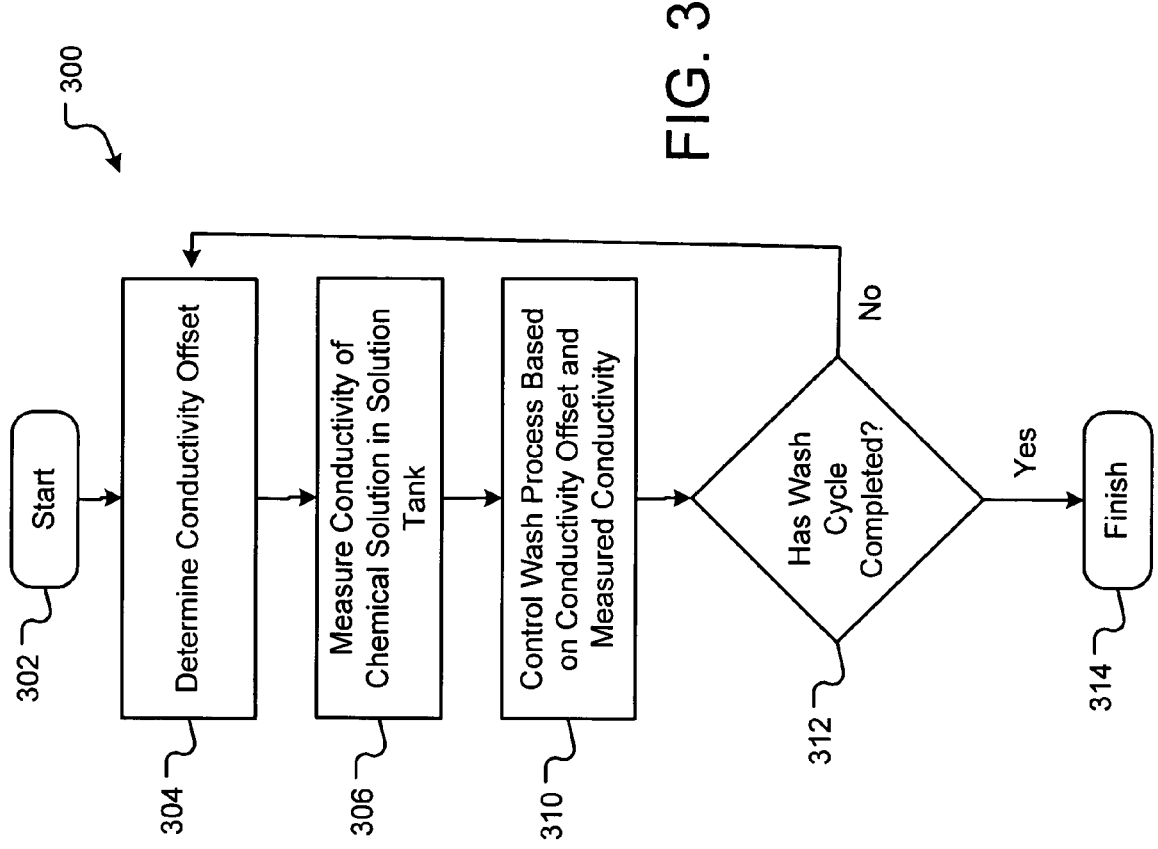
FIG. 3 is a flow diagram that illustrates operational characteristics for controlling application of a component chemical product for use in forming a chemical solution being used by a utility device in accordance with an embodiment of the present invention.

With the computing environment in mind, FIG. 3 illustrates operational characteristics of a process 300 for controlling the dispensing of a component chemical product for use in forming a chemical solution being used by a utility device in accordance with an embodiment of the present invention. The chemical solution is formed by dissolving the component chemical product in water in a solution tank. For illustrative purposes, and not by means of limitation, the "control" process 300 is described below as a process for controlling operations associated with the warewash machine 100 of FIG. 1 during a wash cycle. In this embodiment, the logical operations of the control process 300 are performed by the controller resident in the control box 112.

The control process 300 is performed with an operation flow beginning with a start operation 302 and concluding with a terminate operation 314. The start operation 302 is initiated at the beginning of each wash cycle that occurs after the warewash machine 100 has been deployed in an environment in which the machine 100 is intended for use. As such, the control process 300 is initiated after a field service technician has activated the controller for use in the environment by means such as commands input through the GUI 122. After the start operation 302 has been triggered by detection of a wash cycle, the operation flow passes to a determine offset operation 304.

The determine offset operation 304 determines a conductivity offset that is to be applied to conductivity measurements derived by sampling the chemical solution contained in the solution tank 140 during the wash cycle. In accordance with an embodiment of the present invention, the conductivity offset represents a portion of the derived conductivity measurement that is attributable to the water used to form the chemical solution. A process for determining a conductivity offset in accordance with this embodiment (i.e., "water offset") is described below with reference to FIG. 5. In another embodiment, the conductivity offset represents an estimated portion of the derived conductivity measurement that is attributable to any soils that may exist in the chemical solution. A process for determining a conductivity offset in accordance with this embodiment (i.e., "soil offset") is described below with reference to FIG. 6. Finally, in accordance with yet another embodiment, the conductivity offset represents a combination of the portion of the derived conductivity measurement that is attributable to the water used to form the chemical solution and the estimated portion of the derived conductivity measurement attributable to any soils that may exist in the chemical solution. In this embodiment, the conductivity offset is determined by adding the water offset determined in accordance with the process of FIG. 5 to the soil offset determined in accordance with the process of FIG. 6.

Figure 7:
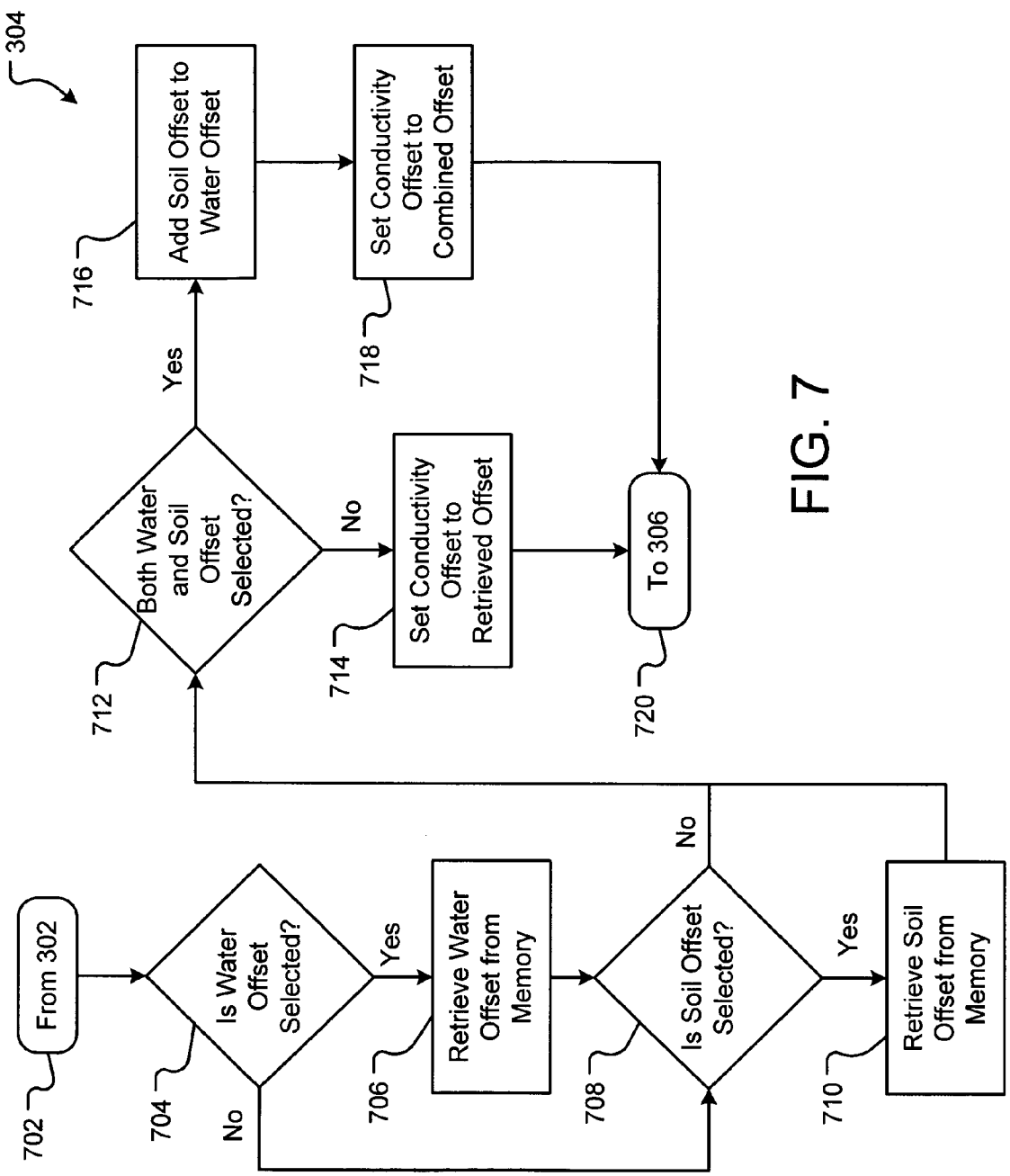
FIG. 7 is a flow diagram that illustrates operational characteristics shown in FIG. 3 in more detail in accordance with an embodiment of the present invention.

The determine offset operation 304 determines whether to use a water offset, a soil offset or both based on instructions input to the controller through the GUI 122. As such, the offset that is to be used by the control process 300 to control dispensing of the component chemical product is based on operator preferences. These operator preferences are preferably input by a field service technician during deployment of the warewash machine 100 into the operational environment, and further, may be modified by the operator during operation of the machine 100 in this environment. The determine offset operation 304 determines the conductivity offset based on the current operator settings defined for the warewash machine 100 at the start of the wash cycle that initiates the control process 300 at the start operation 302. FIG. 7, described below, illustrates in more detail the logical process of the determine offset operation 304 to render the conductivity offset in accordance with an embodiment of the present invention.

After the conductivity offset is determined, the operation flow for the control process 300 passes to a sense conductivity operation 306. The sense conductivity operation 306 gathers samples of the chemical solution over a predetermined period in time, and using these samples, measures the conductivity of the chemical solution in multiple instances (for each sample) during the predetermined period in time. These conductivity measurements are averaged to render an average conductivity reading for the predetermined period in time. As noted above, these conductivity measurements, and thus the average thereof, are indicative of the percent concentration of the component chemical product in the chemical solution. In an embodiment, the memory of the controller includes a data structure, e.g., table, formula, etc., for matching all possible conductivity readings for the chemical solution to an associated percent concentration of the component chemical product relative to the component water. This data structure is used, for example, to display the current percent concentration of component chemical product in the solution on the GUI 122 for display to operators of the warewash machine 100. After the average conductivity reading for the predetermined period in time is determined, the operation flow passes to a control operation 310.

The control operation 310 renders control decisions relative to component chemical product dispensing based on an analysis of the average conductivity reading for the chemical solution against a conductivity setpoint, taking into consideration the conductivity offset determined in the determine offset operation 304. To accomplish this, the control operation either "normalizes" the conductivity setpoint or the average conductivity reading based on the conductivity offset, as described in greater detail in accordance with an embodiment of the present invention described below with reference to FIG. 4.

The control operation 310 analyzes the average conductivity reading against the conductivity setpoint, one of which is "normalized," by comparing these two values to determine whether the reading is less than the setpoint. In response to determining that the reading is less than the setpoint, the control operation 310 commands the processor for the product dispense reservoir 110 to dispense a specified quantity of the component chemical product to the solution tank 140. This specified quantity is derived based on the relative discrepancy between the reading and the conductivity setpoint, again, one of which is normalized. From the control operation 310, the operation flow passes to a query operation 312. The query operation 312 determines whether the wash cycle has completed. If the wash cycle has completed, the operation flow concludes at the terminate operation 314. Otherwise, the operation flow passes back to the determine offset operation 304 and continues as previously described.

Figure 4:
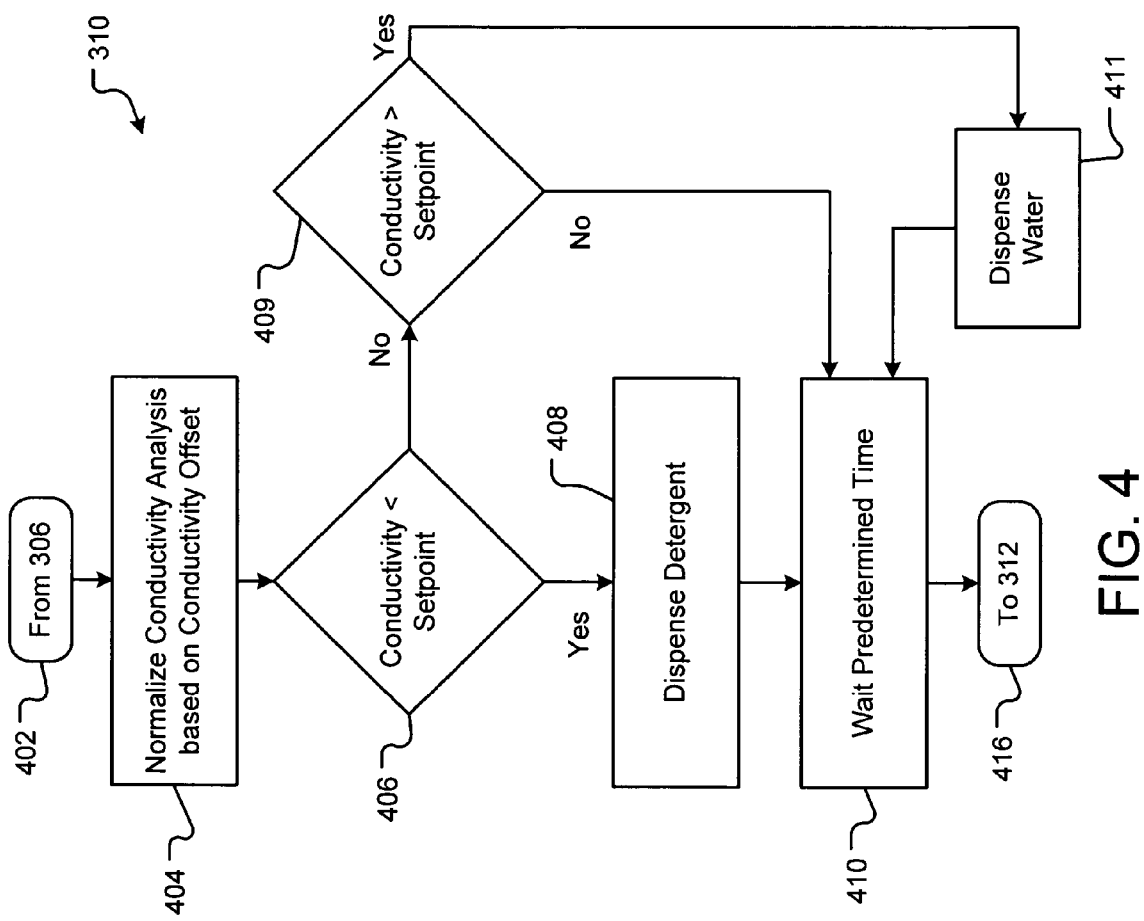
FIG. 4 is a flow diagram that illustrates operational characteristics shown in FIG. 3 in more detail in accordance with an embodiment of the present invention.

Turning now to FIG. 4, operational characteristics of the control operation 310 of FIG. 3 are shown in accordance with an embodiment of the present invention. Specifically, these operational characteristics include an ingress operation 402 that accepts the operation flow of the control process 300 following conclusion of the sense conductivity operation 306 (FIG. 3) and an egress operation 416 that passes the operation flow of the control process 300 to the query operation 312 (FIG. 3). From the ingress operation 402, the operation flow continues to a normalize operation 404.

In a first embodiment, the normalize operation 404 determines an "normalized" conductivity reading for the chemical solution by subtracting the conductivity offset from the average conductivity reading for the chemical solution. As such, the average conductivity reading for the chemical solution is "normalized" based on the conductivity offset. In a second embodiment, the normalize operation 404 normalizes the conductivity setpoint for the chemical solution rather than the average conductivity reading. In this embodiment, the normalize operation 404 adds the conductivity offset to the conductivity setpoint to render a "normalized" conductivity setpoint.

Regardless of the embodiment, the operation flow passes from the normalize operation 404 to a second query operation 406. The second query operation 406 analyzes the relationship of the conductivity of the chemical solution to the conductivity setpoint. If the normalize operation 404 normalized the average conductivity reading for the chemical solution to the conductivity offset, then the second query operation 406 determines whether the normalized conductivity measurement is less than the conductivity setpoint. Likewise, if the normalize operation 404 normalized the conductivity setpoint to the conductivity offset, then the second query operation 406 determines whether the conductivity reading for the chemical solution is less than the normalized conductivity setpoint. In either case, if the conductivity of the chemical solution is less than the conductivity setpoint, the operation flow passes to a dispense product operation 408. Otherwise, the operation flow passes to a third query operation 409.

The dispense product operation 408 commands the processor for the product dispense reservoir 110 to dispense a specified quantity of component chemical product to the solution tank 140. The specified quantity is based on the relative discrepancy between the conductivity of the chemical solution and the conductivity setpoint, taking into account the conductivity offset. From the dispense product operation 408, the operation flow passes to a pause operation 410.

The third query operation 409 analyzes the relationship of the conductivity of the chemical solution to the conductivity setpoint to determine whether the conductivity of the chemical solution is greater than the conductivity setpoint, taking into account the conductivity offset. If the normalize operation 404 normalized the average conductivity reading for the chemical solution to the conductivity offset, then the third query operation 409 determines whether the "normalized" conductivity measurement is greater than the conductivity setpoint. Likewise, if the normalize operation 404 normalized the conductivity setpoint to the conductivity offset, then the third query operation 409 determines whether the conductivity reading for the chemical solution is greater than the "normalized" conductivity setpoint. In either case, if the conductivity of the chemical solution is greater than the conductivity setpoint, the operation flow passes to a dispense water operation 411. Otherwise, the operation flow passes to the pause operation 410.

The dispense water operation 411 commands the rinse module 102 to dispense a specified quantity of water to the washing chamber 108. The specified quantity is based on the relative discrepancy between the conductivity of the chemical solution and the target percent concentration, taking into account the conductivity offset. From the dispense water operation 411, the operation flow passes to the pause operation 410.

The pause operation 410 pauses the control process 300 for a predetermined period in time. This predetermined period in time may be either zero to infinite units (e.g., seconds, minutes, days, etc.) and is preferably set by the field service person (via GUI 122) during deployment of the machine 100 in its operational environment. After the predetermined period in time, the operation flow of the control process 300 passes from the pause operation 410 to the egress operation 416. In turn, the egress operation 416 passes the operation flow to the query operation 314, and the control process 300 continues as described above.

Figure 5:
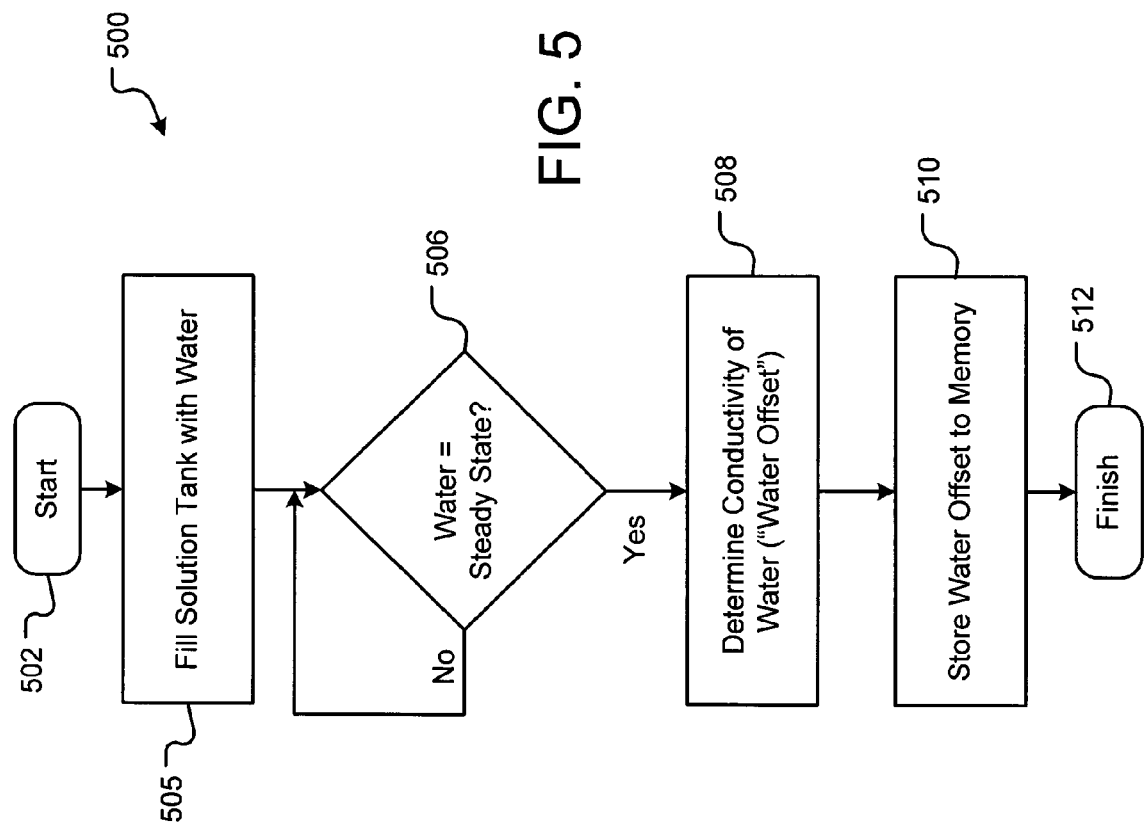
FIG. 5 is a flow diagram that illustrates operational characteristics for determining conductivity attributable to water forming the chemical solution used in the process of FIG. 3 in accordance with an embodiment of the present invention.

Referring now to FIG. 5, a process 500 for determining the water offset for use in the control process of FIG. 3 is shown in accordance with an embodiment of the present invention. As known to those of skill in the art, the inherent conductivity of the water varies based on geographic location of the origin of the water. The hardness-softness of the water, as well as the particles, e.g., ions, minerals, etc., contained within the water play a role in defining the inherent conductivity of the water. Typically, these parameters vary not only over disperse geographic locations, but also based on the source, e.g., well, treatment plant, river/creek bed, etc., of the water. The process 500 (referred to herein as a "water offset determination process 500") provides an accurate means for determining the water offset regardless of the source and geographic origin of the water used to form a chemical solution.

The water offset determination process 500 is administered prior to deployment of the warewash machine 100 in its operational environment. Indeed, the water offset determination process 500 is performed in an operation flow beginning with a start operation 502 and ending with a terminate operation 512, both of which occur in time prior the performance of the control process 300. In an embodiment, the start operation 502 is initiated during setup of the warewash machine 100 in its operational environment by a field service technician requesting initiation of this process 500 through the GUI 122. From the start operation 502, the operation flow of the water offset determination process 500 immediately passes to a fill tank operation 504.

In an embodiment wherein the controller controls operation of the rinse module 102, the fill tank operation 504 controls the application of water to the solution tank 140 such that the inductive probe 138 is covered by the water. In an embodiment wherein the controller only monitors operation of the rinse module 102, the fill tank operation 504 monitors the application of water to the solution tank 140 to determine when the inductive probe 138 is covered by water. After the level of water in the solution tank 140 rises above the inductive probe 138, the operation flow passes to a query operation 506. The query operation 506 serves as a time delay in the process 500 wherein the process 500 is halted until the water in the solution tank 140 reaches steady state. Steady state is reached when the particles, e.g., ions, minerals, etc., within the water are uniformly dispersed throughout the water in the tank 140. As the water in the tank 140 reaches steady state, the operation flow passes to a determine conductivity operation 508.

The determine conductivity operation 508 uses the inductive probe 138 to sense the conductivity of the water at steady state in the solution tank 140. This measurement is repeated a predetermined number of times to render a plurality of conductivity measurements at steady state. Next, the determine conductivity operation 508 averages these conductivity measurements, thereby returning an average conductivity reading for the water at steady state. This average conductivity reading for the water constitutes the "water offset." After the water offset is determined, the operation flow passes to a data store operation 510.

The data store operation 510 saves the water offset to memory within the controller for subsequent use by the determine offset operation 304 described above with reference to the control process 300 of FIG. 3. From the data store operation 510, the operation flow of the offset determination process 500 concludes at the terminate operation 512.

Figure 6:
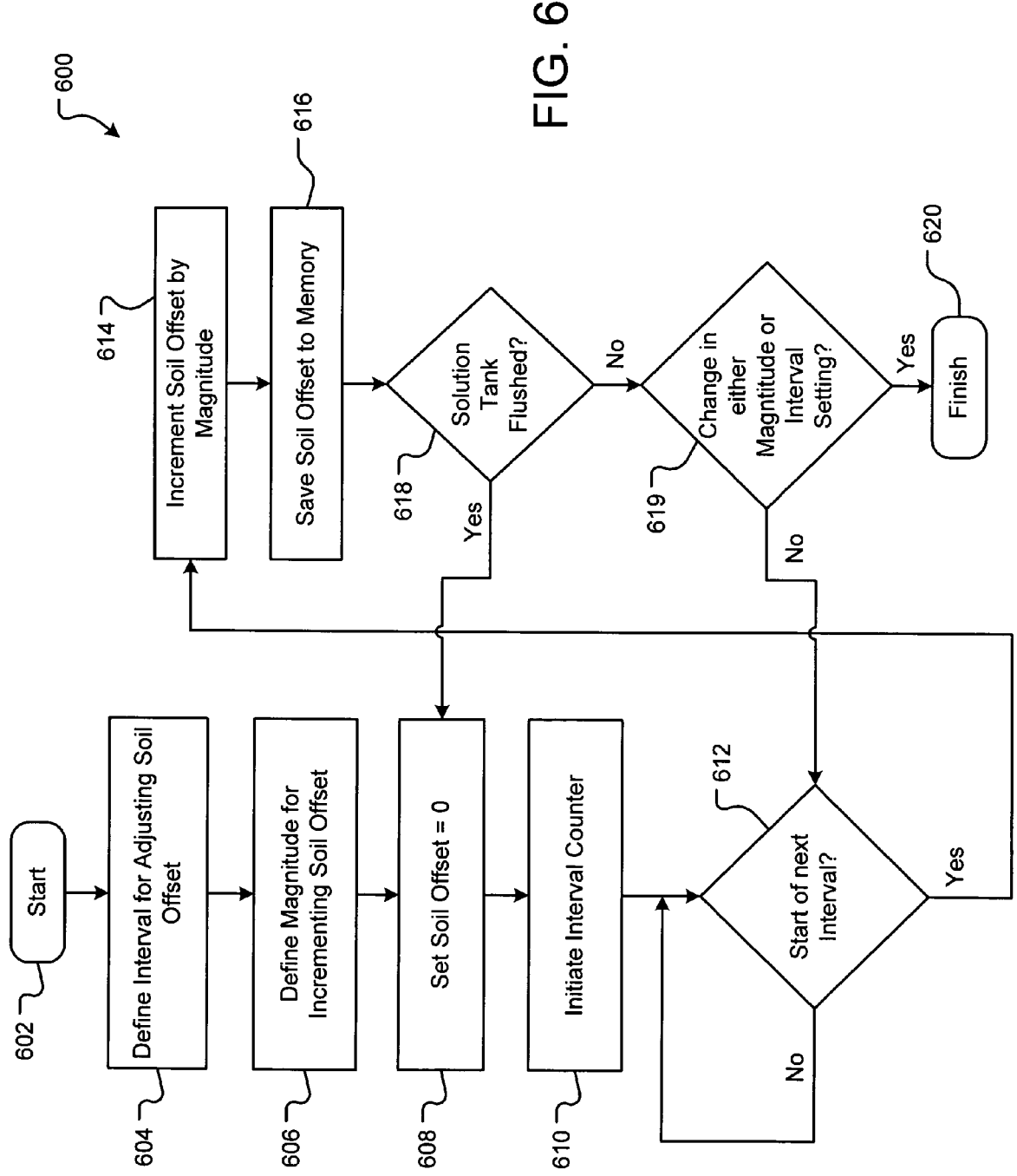
FIG. 6 is a flow diagram that illustrates operational characteristics for determining conductivity attributable to an estimated soil concentration in the chemical solution used in the process of FIG. 3 in accordance with an embodiment of the present invention.

Referring now to FIG. 6, a process 600 for determining the soil offset for use in the control process 300 of FIG. 3 is shown in accordance with an embodiment of the present invention. This process 600 therefore determines the soil offset rendered by the offset determination operation 304 in certain embodiments. While the water offset determination process 500 shown in FIG. 5 is preferably administered during deployment of the warewash machine 100 into its operational environment, this process 600, which is hereinafter referred to as a "soil offset determination process," is continuously administered during the operational life of the machine 100. The soil offset determination process 600 is performed in an operation flow beginning with a start operation 602 and ending with a finish operation 620.

The start operation 602 is initiated in response to an operator or field service person requesting that a soil offset be established and used to control the percent concentration of a component chemical product in a chemical solution used in warewash processes of the warewash machine 100. Such a request is preferably input by the operator or field service person to the controller through the GUI 122. Further, this request may be made during deployment of the machine 100 into its operational environment, or alternatively, during normal operation of the machine 100, in which case, the operator's request is to modify a current setting affecting the soil offset, such as the interval and magnitude setting described below. In an embodiment, the controller receives this request and triggers initiation of the operation flow of the soil offset determination process 600 at the start operation 602. From the start operation 602, the operation flow passes to the define interval operation 604.

As noted above, the soil offset is attributable to soils that may wash off articles in the washing chamber 108 and into the solution tank 140. The expected accumulation of soil in the solution tank 140 increases following each rack washed by the warewash machine 100. Consequently, so does the portion of the conductivity of the chemical solution attributable to the soil. The define interval operation 604 addresses this expected increase in conductivity by accepting from a user and storing to memory an interval setting that will be used by subsequent operations in this soil offset determination process 600 to determine when the soil offset is to be increased by a specified magnitude intended to track the soil accumulation in the solution tank 140.

In a first embodiment, the interval is based on a predetermined number of racks that may be supplied to the warewash machine 100 without increasing the soil offset. For example, the interval may be five (5) racks. After each set of five (5) racks is supplied to the warewash machine 100, the soil offset is increased by the specified magnitude. In a second embodiment, the interval is based on a factor of time, e.g., seconds, minutes, hours and days, and as such, the interval defines the length of a time period that will be used to trigger an increase in the soil offset by the specified magnitude. For example, the interval may dictate that the soil offset be increased by the specified magnitude every 5 minutes that the wash module 106 is active (i.e., dispensing solution). Of course, interval considerations other than rack count and time factors are contemplated within the scope of the present invention.

Regardless of the type (e.g., time, rack count, etc.), the relative duration of the interval is a matter of choice taking into consideration the subjective practices of the operational environment in which the warewash machine 100 is deployed. For example, an operational environment in which the soil load of articles washed by the warewash machine 100 is heavy may have a shorter interval than an operational environment associated with light soil loads. More specifically, while the former is best suited for an interval or 3 racks, or alternatively 5 minutes, the latter may be best suited for an interval of 9 racks, or 15 minutes. Numerous approximation methods may be used to render an interval for a specific operational environment, such as analyzing the historical practices of the environment as well as laboratory tests (e.g., trial and error). Once determined, the interval is input into the controller by an operator or field service technician through the GUI 122 and accepted into the soil offset determination process 600 at the define interval operation 604. The define interval operation 604 then stores the accepted interval into memory for subsequent use in the process 600. From the define interval operation 604, the operation flow passes to a define magnitude operation 606.

The define magnitude operation 604 accepts from a user (e.g., operator, field service technician, etc.) and stores to memory a magnitude setting that will be used by subsequent operations in this soil offset determination process 600 as the specified magnitude by which the soil offset is to be increased at the beginning of each interval. Like the interval setting described above, the actual magnitude is a matter of choice taking into consideration the subjective practices of the operational environment in which the warewash machine 100 is deployed. Indeed, the same factors and analyses that may be used to derive the interval may also be used to derive this magnitude. From the define magnitude operation 604, the operation flow passes to an initialize operation 608.

The initialize operation 608 initializes the soil offset to a magnitude of zero (0) and then passes the operation flow to the initiate counter operation 610. The initiate counter operation 610 initiates an interval counter relative to the interval setting defined in define interval operation 604. For example, with respect to the first described embodiment, the interval counter represents a count of how many racks have passed through the warewash machine 100 since initiation of the start operation 602. In this embodiment, the initiate counter operation 610 sets the interval counter to zero (0) racks. With respect to the second described embodiment, the interval counter represents a clock that references an amount of time that a particular component in the warewasher has been active since the initiation of the start operation 602. In this embodiment, the initiate counter operation 610 sets the interval counter to a zero (0) time format (e.g., 00:00:00). From the initiate counter operation 610, the operation flow passes to a first query operation 612.

The first query operation 612 serves as a timing loop that waits for the start of the next interval. For example, if the interval is based on a specified number of racks, then the operation flow of the soil offset determination process 600 is maintained at the first query operation 612 until the specified number of racks 102 has been washed by the warewash machine 100. Upon detecting the start of the next interval, the first query operation 612 passes the operation flow to the increment soil offset operation 614.

The increment soil offset operation 614 increments the soil offset by the magnitude defined in the define magnitude operation 606 such that the resulting soil offset reflects the estimated accumulation of soil washed from articles in the washing chamber 108 into the solution tank 140 since the beginning of the previous interval. From the increment soil offset operation 614, the operation flow passes to a storage operation 616. The storage operation 616 replaces any soil offset value currently saved in memory with the soil offset value resulting from the magnitude increase by the increment soil offset operation 614. As such, this updated soil offset value is ready for subsequent use by the determine offset operation 304 described above with reference to the control process 300 of FIG. 3. From the storage operation 616, the operation flow passes to a second query operation 618.

The second query operation 618 queries whether the chemical solution in the solution tank 140 has been flushed from the warewash machine 100. If the solution has been flushed from the machine 100, the second query operation 618 passes the operation flow back to the initialize operation 608, which resets the soil offset to a magnitude of zero (0). It is assumed that the controller concurrently directs the rinse module and the component chemical product dispenser to form a fresh volume of chemical solution in the solution tank 140, as performed during initialization of the machine 100 while being deployed in its operational environment. From the initialize operation 608, the operation flow continues as described above. If, however, the solution has not been flushed from the machine 100, the second query operation 618 passes the operation flow to a third query operation 619.

As noted above, the interval and magnitude settings may be modified during operation of the warewash machine 100. The third query operation 619 determines whether such a modification has been administered since the activation of the soil offset determination process 600 process at the start operation 602. If neither the magnitude or interval settings have been modified, the third query operation 619 passes the operation flow back to the first query operation 612 and the soil offset determination process 600 continues as described above. However, if any such modifications are detected, the third query operation 619 terminates the soil offset determination process 600 by passing the operation flow to the finish operation 620. Consequently, the operation flow of the soil offset determination process 600 will be re-initiated at the start process 602 such that the modified settings may be defined in the controller by the define offset operation 604 and/or the define magnitude operation 606. In this embodiment, the soil offset determination process 600 is re-initiated under the assumption that the chemical solution in the solution tank will be drained at least prior to passage of the operation flow to the initialize operation 608. In an alternative embodiment, the appropriate define operation(s) (304 and/or 306) may be performed without terminating the current operation flow, and the offset determination process 600 may continue without the solution tank 140 being flushed. Such an embodiment may be particularly useful in operational environments in which an operator notices that the chemical solution is accumulating an extraordinary amount of soil relative to the accumulation on which the current interval and/or magnitude setting(s) is/are based, but does not have the time or luxury to flush the machine 100.

Referring now to FIG. 7, operational characteristics of the offset determination operation 304 of FIG. 3 are shown in accordance with an embodiment of the present invention. Specifically, these operational characteristics include an ingress operation 702 that accepts the operation flow of the control process 300 from the start operation 302 (FIG. 3) and an egress operation 720 that passes the operation flow of the control process 300 to the sense conductivity operation 306 (FIG. 3). From the ingress operation 702, the operation flow passes to a first query operation 704. The first query operation 704 determines whether the current operator settings specify that the conductivity analysis is to be normalized based on water offset, and if so, passes the operation flow to a water offset retrieval operation 706. Otherwise, the first query operation 704 passes the operation flow to a second query operation 708.

The water offset retrieval operation 706 retrieves the water offset value from the location in memory to which the water offset was stored by storage operation 510. From the water offset retrieval operation 706, the operation flow passes to the second query operation 708. The second query operation 708 determines whether the current operator settings specify that the conductivity analysis is to be normalized based on soil offset, and if so, passes the operation flow to a soil offset retrieval operation 710. Otherwise, the second query operation 708 passes the operation flow to a third query operation 712.

The soil offset retrieval operation 710 retrieves the soil offset value from the location in memory to which the soil offset was stored by storage operation 616. As such, the soil offset retrieval operation 710 accesses the most current value of the soil offset, which as noted above, is dynamically modified based on a specified time interval. From the soil offset retrieval operation 710, the operation flow passes to the third query operation 712. The third query operation 712 determines whether the current operator settings specify that the conductivity analysis is to be normalized based on both the soil offset and the water offset, and if so, passes the operation flow to a combined offset determination 716. Otherwise, the third query operation 712 passes the operation flow to a first offset definition operation 714. The first offset definition operation 714 sets the conductivity offset value to be used by the control process 300 to the retrieved offset value, i.e., either (1) the soil offset value retrieved by the soil offset retrieval operation 710; or (2) the water offset value retrieved by the water offset retrieval operation 706.

Following the "yes" branch from the third query operation 712, the combined offset determination 716 adds the soil offset value retrieved by the soil offset retrieval operation 710 to the water offset value retrieved by the water offset retrieval operation 706 to render a total (combined) offset value. The operation flow then passes to a second offset definition operation 718, which sets the conductivity offset value to be used by the control process 300 to the total (combined) offset value. From both the first (714) and second (718) offset definition operations, the operation flow passes to the egress operation 720. In turn, the egress operation 720 passes the operation flow to the sense conductivity operation 306. The operation flow of the control process 300 thereafter continues as described above with the conductivity offset value that will be used by the control operation 310 being the value set by either the first offset definition operation 714 or the second offset determination operation 718.

It will be clear that the present invention is well adapted to attain the ends and advantages mentioned, as well as those inherent therein. While a presently preferred embodiment has been described for purposes of this disclosure, various changes and modifications may be made which are well within the scope of the present invention. For example, the controller in the control box 112 is described in FIG. 2 as a processor 201, but may be replaced by or include conventional electrical and electronic devices/components, such as, without limitation, programmable logic controllers (PLC's) and logic components. In these embodiments, the logical operations of the present invention described in FIGS. 3, 4, 5, 6 and 7 are administered by these conventional electrical and electronic devices/components.

In accordance with yet another embodiment, the controller connects to a communications network by way of a network interface, such as the network adapter 211 shown in FIG. 2. Through this network connection, the controller is operable to transmit information to one or more remote computers, such as, without limitation, a server computer or user terminals. Various types of information may be transmitted from the controller to these remote computers over the network connection including, without limitation, data related to the analysis of the conductivity measurements against the conductivity setpoint in both embodiments where either parameter is normalized by the conductivity offset, the average conductivity measurements, the conductivity setpoint for various component chemical products used by the utility device controlled by the controller, the measured conductivity offsets for water, etc. In addition, the network adaptor 211 enables users at remote computers the ability to issue commands to the controller. For example, a user at a remoter computer may modify the conductivity setpoint using this network connection.

Numerous other changes may be made which will readily suggest themselves to those skilled in the art and which are encompassed in the spirit of the invention disclosed and as defined in the appended claims.

What is claimed is:

1. In a computer system, a method for controlling concentration of a component chemical product in a chemical solution, the method comprising:

determining a conductivity measurement for the chemical solution, wherein the conductivity measurement indicates a percent concentration of the component chemical product in the chemical solution;

determining a conductivity offset value that represents a portion of the conductivity measurement that is attributable to one or more constituents of the chemical solution other than the component chemical product; and analyzing the conductivity offset value, the conductivity measurement and a conductivity setpoint indicating a desired percent concentration of the component chemical product in the chemical solution to determine whether the component chemical product should be added to the chemical solution.

2. A method as defined in claim 1, wherein the chemical solution is formed by combining the component chemical product with water in a solution tank and used by a utility device to clean and sanitize articles having soil deposited thereon, wherein the utility device applies the chemical solution to the articles thereby washing the soil and applied chemical solution into the solution tank, the determining act comprising:

determining a soil conductivity offset value that represents a portion of the conductivity measurement that is attributable to soil mixed into the chemical solution;

determining a water conductivity offset value that represents a portion of the conductivity measurement that is attributable to water used to form the chemical solution; and adding the soil conductivity offset value and the water conductivity offset value to render the conductivity offset value.

3. A method as defined in claim 2, wherein the analyzing act comprises:

subtracting the conductivity offset value from the conductivity measurement to render a normalized conductivity reading for the chemical solution; and comparing the normalized conductivity reading of the chemical solution to the conductivity setpoint.

4. A method as defined in claim 3, wherein the analyzing act comprises:

adding the conductivity offset value to the conductivity setpoint to render an normalized conductivity setpoint for the chemical solution; and comparing the conductivity measurement of the chemical solution to the normalized conductivity setpoint.

5. A method as defined in claim 4, further comprising:

prior to supplying the component chemical product to the solution storage tank, filling the solution storage tank with water and analyzing one or more samples of the water to generate the water conductivity offset value.

6. A method as defined in claim 5, further comprising:

after the water conductivity offset value has been determined by the analyzing act, supplying the component chemical product to the solution storage tank to begin formation of the chemical solution therein, wherein the act of determining a conductivity measurement for the chemical comprises analyzing one or more samples of the chemical solution to generate the conductivity measurement.

7. A method as defined in claim 6, wherein the chemical solution is flushed from the solution tank after a predetermined period in time, the method further comprising:

defining an interval for adjusting the soil conductivity offset value, wherein the interval represents periods in time that the soil conductivity offset value is to be maintained at a constant value;

setting the soil conductivity offset value to an initial value during an initial period in time conforming to the interval, wherein the initial period in time begins concurrently with the predetermined period in time; and increasing the soil conductivity offset value by a specified magnitude at each of a subsequent periods in time conforming to the interval.

8. A method as defined in claim 7, further comprising:

storing the increased soil conductivity offset value to a location in a memory such that any previous soil conductivity offset value in the location is overwritten by the increased soil conductivity offset value, wherein act of determining the soil conductivity offset value comprises retrieving the soil conductivity offset value from the memory location for use by the analyzing act.

9. In a computer system, a method for controlling conductivity of a chemical solution contained in a solution tank and used by a utility device to clean and sanitize articles having soil deposited thereon, wherein the utility device applies the chemical solution to the articles thereby washing the soil and applied chemical solution into the solution tank, the method comprising:

determining a conductivity measurement for the chemical solution, wherein the conductivity measurement indicates a percent concentration of a component chemical product in the chemical solution;

determining a soil conductivity offset value that represents a portion of the conductivity measurement that is attributable to soil mixed into the chemical solution; and analyzing the soil conductivity offset value, the conductivity measurement and a conductivity setpoint indicating a desired percent concentration of the component chemical product in the chemical solution to determine whether the component chemical product should be added to the chemical solution.

10. A method as defined in claim 9, wherein the analyzing act comprises:

subtracting the soil conductivity offset value from the conductivity measurement to render a normalized conductivity reading for the chemical solution; and comparing the normalized conductivity reading of the chemical solution to the conductivity setpoint.

11. A method as defined in claim 10, further comprising:
if the normalized conductivity reading for the chemical solution is less than the conductivity setpoint, requesting that a specified volume of component chemical product be supplied to the solution tank.

12. A method as defined in claim 11, wherein the specified volume is defined based on a relative discrepancy between the normalized conductivity reading and the conductivity setpoint.

13. A method as defined in claim 11, wherein the specified volume is a predetermined volume that is to be supplied to the solution storage tank each time the normalized conductivity reading of the chemical solution is less than the conductivity setpoint.

14. A method as defined in claim 11, further comprising:
if the normalized conductivity reading for the chemical solution is greater than the conductivity setpoint, requesting that a specified volume of water be supplied to the solution tank.

15. A method as defined in claim 14, wherein the specified volume of water is defined based on a relative discrepancy between the conductivity measurement and the normalized conductivity reading.

16. A method as defined in claim 9, wherein the analyzing act comprises:

adding the soil conductivity offset value to the conductivity setpoint to render an normalized conductivity setpoint for the chemical solution; and comparing the conductivity measurement of the chemical solution to the normalized conductivity setpoint.

17. A method as defined in claim 16, further comprising:
if the conductivity measurement of the chemical solution is less than the normalized conductivity setpoint, requesting that a specified volume of component chemical product be supplied to the solution tank.

18. A method as defined in claim 17, wherein the specified volume is defined based on a relative discrepancy between the conductivity measurement and the normalized conductivity setpoint.

19. A method as defined in claim 17, wherein the specified volume is a predetermined volume that is to be supplied to the solution tank each time the conductivity measurement of the chemical solution is less than the normalized conductivity setpoint.

20. A method as defined in claim 17, further comprising:
if the conductivity measurement of the chemical solution is greater than the normalized conductivity setpoint, requesting that a specified volume of water be supplied to the solution tank.

21. A method as defined in claim 20, wherein the specified volume of water is defined based on a relative discrepancy between the conductivity measurement and the normalized conductivity setpoint.

22. A method as defined in claim 9, further comprising:
transmitting at least one of the conductivity measurement for the chemical solution and the soil conductivity offset value to a remote computer over a network connection.

23. A method as defined in claim 9, further comprising:
transmitting results rendered by the analyzing act to a remote computer over a network connection.

24. A method as defined in claim 9, wherein the chemical solution is flushed from the solution tank after a predetermined period in time, the method further comprising:

defining an interval for adjusting the soil conductivity offset value, wherein the interval represents periods in time that the soil conductivity offset value is to be maintained at a constant value;

setting the soil conductivity offset value to an initial value during an initial period in time conforming to the interval, wherein the initial period in time begins concurrently with the predetermined period in time; and increasing the soil conductivity offset value by a specified magnitude at each of a subsequent periods in time conforming to the interval.

25. A method as defined in claim 24, further comprising:
storing the increased soil conductivity offset value to a location in a memory such that any previous soil conductivity offset value in the location is overwritten by the increased soil conductivity offset value, wherein act of determining the soil conductivity offset value comprises retrieving the soil conductivity offset value from the memory location for use by the analyzing act.

26. A method as defined in claim 24, wherein the interval represents a period in time between detection of a first article rack carrying articles for washing by the utility device and a second article rack carrying articles for washing by the utility device.

27. A method as defined in claim 24, wherein the interval represents a period in time derived from a clock count.

28. A method as defined in claim 24, further comprising:
repeating the setting act at the conclusion of the predetermined period in time such that the soil conductivity offset value is returned to the initial value after the solution tank has been flushed.

29. A computer program storage device accessible to a computing system and encoding a computer program for executing a computer process for controlling conductivity of a chemical solution contained in a solution tank and used by a utility device to clean and sanitize articles having soil deposited thereon, wherein the utility device applies the chemical solution to the articles thereby washing the soil and applied chemical solution into the solution tank, the method comprising:

determining a conductivity measurement for the chemical solution, wherein the conductivity measurement indicates a percent concentration of a component chemical product in the chemical solution;

determining a soil conductivity offset value that represents a portion of the conductivity measurement that is attributable to soil mixed into the chemical solution; and analyzing the soil conductivity offset value, the conductivity measurement and a conductivity setpoint indicating a desired percent concentration of the component chemical product in the chemical solution to determine whether the component chemical product should be added to the chemical solution.

30. A computer program storage device as defined in claim 29, wherein the analyzing act comprises:

subtracting the soil conductivity offset value from the conductivity measurement to render a normalized conductivity reading for the chemical solution; and comparing the normalized conductivity reading of the chemical solution to the conductivity setpoint.

31. A computer program storage device as defined in claim 29, wherein the analyzing act comprises:

adding the soil conductivity offset value to the conductivity setpoint to render an normalized conductivity setpoint for the chemical solution; and comparing the conductivity measurement of the chemical solution to the normalized conductivity setpoint.

32. A computer program storage device as defined in claim 29, further comprising:

transmitting at least one of the conductivity measurement for the chemical solution and the soil conductivity offset value to a remote computer over a network connection.

33. A computer program storage device as defined in claim 29, further comprising:

transmitting results rendered by the analyzing act to a remote computer over a network connection.

34. A computer program storage device as defined in claim 29, wherein the chemical solution is flushed from the solution tank after a predetermined period in time, the method further comprising:

defining an interval for adjusting the soil conductivity offset value, wherein the interval represents periods in time that the soil conductivity offset value is to be maintained at a constant value;

setting the soil conductivity offset value to an initial value during an initial period in time conforming to the interval, wherein the initial period in time begins concurrently with the predetermined period in time; and increasing the soil conductivity offset value by a specified magnitude at each of a subsequent periods in time conforming to the interval.

35. A computer program storage device as defined in claim 34, further comprising:

storing the increased soil conductivity offset value to a location in a memory such that any previous soil conductivity offset value in the location is overwritten by the increased soil conductivity offset value, wherein act of determining the soil conductivity offset value comprises retrieving the soil conductivity offset value from the memory location for use by the analyzing act.

36. A computer program storage device as defined in claim 35, wherein the interval represents a period in time between detection of a first article rack carrying articles for washing by the utility device and a second article rack carrying articles for washing by the utility device.

37. A computer program storage device as defined in claim 35, wherein the interval represents a period in time derived from a clock count.

38. A computer program storage device as defined in claim 35, further comprising:

repeating the setting act at the conclusion of the predetermined period in time such that the soil conductivity offset value is returned to the initial value after the solution tank has been flushed.

39. A computer program storage device accessible to a computing system and encoding a computer program for executing a computer process for controlling conductivity of a chemical solution, the method comprising:

determining a conductivity measurement for the chemical solution, wherein the conductivity measurement indicates a percent concentration of a component chemical product in the chemical solution;

determining a conductivity offset value that represents a portion of the conductivity measurement that is attributable to a component of the chemical solution other than the component chemical product; and analyzing the conductivity offset value, the conductivity measurement and a conductivity setpoint indicating a desired percent concentration of the component chemical product in the chemical solution to determine whether the component chemical product should be added to the chemical solution.

40. A computer program storage device as defined in claim 39 wherein the chemical solution is formed by combining the component chemical product with water in a solution tank and used by a utility device to clean and sanitize articles having soil deposited thereon, wherein the utility device applies the chemical solution to the articles thereby washing the soil and applied chemical solution into the solution tank, the determining act comprising:

determining a soil conductivity offset value that represents a portion of the conductivity measurement that is attributable to soil mixed into the chemical solution;

determining a water conductivity offset value that represents a portion of the conductivity measurement that is attributable to water used to form the chemical solution; and adding the soil conductivity offset value and the water conductivity offset value to render the conductivity offset value.

* * * * *